United States Patent [19]

Founds et al.

[11] Patent Number: 5,744,318
[45] Date of Patent: Apr. 28, 1998

[54] MONOCLONAL ANTIBODY FOR THE DETECTION OF ADVANCED GLYCOSYLATION ENDPRODUCTS IN BIOLOGICAL SAMPLES

[75] Inventors: Henry W. Founds, Mendham; Homayoun Sadeghi, Sparta, both of N.J.

[73] Assignee: Alteon Inc., Ramsey, N.J.

[21] Appl. No.: 367,507

[22] Filed: Dec. 30, 1994

[51] Int. Cl.$^6$ .............. C07K 16/44; C12Q 1/28; G01N 33/53
[52] U.S. Cl. .......... 435/7.92; 435/7.93; 435/7.94; 435/329; 435/337; 530/387.1; 530/388.1; 530/391.1; 530/387.5; 530/388.25; 530/391.3
[58] Field of Search .............. 530/387.1, 388.1, 530/387.5, 391.1, 391.3, 388.25; 435/7.92, 7.93, 7.94, 329, 337

[56] References Cited

FOREIGN PATENT DOCUMENTS

| WO 93/13421 | 7/1993 | WIPO . |
| WO 94/20083 | 9/1994 | WIPO . |

OTHER PUBLICATIONS

Araki et al., 1992, J. Biol. Chem. 267:10211–14.
Brownlee et al., 1983, J. Exp. Med. 158:1739–1744.
Bucala et al., 1993, Proc. Natl. Acad. Sci. USA 90:6434–38.
Horiuchi et al., 1991, J. Biol. Chem. 266:7329–32.
Kohn et al., 1984, Diabetes 33:57–59.
Makita et al., 1992, J. Biol. Chem. 267:5133–38.
Makita et al., 1992, Science 258:651–653.
Nakayama et al., 1989, Biochem. Biophys. Res. Commun. 162:740–745.

*Primary Examiner*—Frank C. Eisenschenk
*Attorney, Agent, or Firm*—Klauber & Jackson

[57] ABSTRACT

The present invention relates to monoclonal antibodies to advanced glycosylation endproducts formed in vivo and cross-reactive with advanced glycosylation endproducts formed in vitro, and to methods of diagnosis and therapy based thereon. More particularly, the invention is directed to a monoclonal antibody, or an antigen-binding fragment thereof, reactive with in vivo produced advanced glycosylation endproducts (AGEs), which monoclonal antibody or antigen binding fragment thereof demonstrates an immunological binding characteristic of monoclonal antibody 4G9 as produced by hybridoma 4G9, deposited with the American Type Culture Collection (ATCC) and assigned Accession Number CRL 11626. In a specific embodiment, the 4G9 antibody is used in a sandwich ELISA to detect ApoB-AGE, IgG-AGE, collagen-AGE, serum-AGE peptides and proteins and urinary-AGE peptides and proteins.

23 Claims, 5 Drawing Sheets

MONOCLONAL ANTIBODY FOR THE DETECTION OF ADVANCED GLYCOSYLATION ENDPRODUCTS IN BIOLOGICAL SAMPLES

FIELD OF THE INVENTION

The present invention relates to monoclonal antibodies to advanced glycosylation endproducts and methods of diagnosis and therapy based thereon.

BACKGROUND OF THE INVENTION

The present invention relates generally to the detection and measurement of nonenzymatically glycosylated proteins, and particularly to methods and associated materials for the detection and measurement of proteins that have been nonenzymatically glycosylated in vivo.

In the past, notable differences have been observed between the reactivity, chemical identity and immunological characteristics of advanced glycosylation endproducts which are produced in vivo and certain model AGEs which have been characterized over the past several years.

Advanced Glycosylation Endproducts (AGEs)

The reaction between glucose and proteins has been known for some time. Its earliest manifestation was in the appearance of brown pigments during the cooking of food. In 1912, Maillard observed that glucose or other reducing sugars react with amino acids to form adducts that undergo a series of dehydrations and rearrangements to form stable brown pigments (Maillard, 1912, C.R. Acad. Sci. 154:66–68).

In the years that followed the initial discovery by Maillard, food chemists studied the hypothesized reaction in detail and determined that stored and heat-treated foods undergo nonenzymatic browning as a result of the reaction between glucose and polypeptide chains, and that the proteins thereby become crosslinked and exhibit decreased bio-availability. At this point, it was determined that the pigments responsible for the development of the brown color that develops as a result of protein glycosylation possessed characteristic spectra and fluorescent properties; however, the chemical structure of the pigments had not been specifically elucidated.

The reaction between reducing sugars and food proteins discussed above was found in recent years to have its parallel in vivo. Thus, the nonenzymatic reaction between glucose and the free amino groups on proteins to form a stable amino, 1-deoxy ketosyl adduct, known as the Amadori product, has been shown to occur with hemoglobin, wherein a rearrangement of the amino terminal of the β-chain of hemoglobin by reaction with glucose forms an adduct and gives a product known as hemoglobin $A_{1c}$. Similar reactions have also been found to occur with a variety of other body proteins, such as lens crystallin, collagen and nerve proteins (see Bunn et al., 1975, Biochem. Biophys. Res. Commun. 67:103–109; Koenig et al., 1975, J. Biol. Chem. 252:2992–2997; Monnier and Cerami, in *Maillard Reaction in Food and Nutrition*, ed. Waller, G. A., American Chemical Society 1983, pp. 431–448; and Monnier and Cerami, 1982, Clinics in Endocrinology and Metabolism 11:431–452).

Moreover, brown pigments with spectral and fluorescent properties similar to those of late-stage Maillard products have also been observed in vivo in association with several long-lived proteins, such as lens proteins and collagen from aged individuals. An age-related linear increase in pigment was observed in human dura collagen between the ages of 20 to 90 years (see Monnier and Cerami, 1981, Science 211:491–493; Monnier and Cerami, 1983, Biochem. Biophys. Acta 760:97–103; and Monnier et al., 1984, "Accelerated Age-Related Browning of Human Collagen in Diabetes Mellitus", Proc. Natl. Acad. Sci. USA 81:583–587). Interestingly, the aging of collagen can be mimicked in vitro in a much shorter period of time by crosslinking and other non-enzymatic glycosylation (or glycation) reactions induced by incubation of proteins and other biomolecules (e.g. DNA and phospholipids) in solution with relatively high concentrations of glucose. The capture of other proteins and the formation of certain intramolecular adducts on collagen, also noted, is theorized to occur by a crosslinking reaction, and is believed to account, for instance, for the observed accumulation of albumin and antibodies in kidney basement membrane (see Brownlee et al., 1983, J. Exp. Med. 158:1739–1744; and Kohn et al., 1984, Diabetes 33:57–59).

Glucose and other reducing sugars attach non-enzymatically to the amino groups of proteins in a concentration-dependent manner. Over time, these initial Amadori adducts can undergo further rearrangements, dehydrations and cross-linking with other protein groups to accumulate as a family of complex structures referred to as Advanced Glycosylation Endproducts (AGEs). Substantial progress has been made toward the elucidation of the biological roles and clinical significance of advanced glycosylation endproducts, so that it is now acknowledged that many of the conditions heretofore attributed to the aging process or to the pathological effects of diseases such as diabetes, are attributable at least in part to the formation, accumulation and/or activity of AGEs in vivo.

As noted above, advanced glycosylation endproducts tend to accumulate on molecules with long half-lives, especially under conditions of relatively high sugar concentration. Thus, AGE accumulation can be indicative of protein half-life, sugar concentration, or both. These factors have important consequences. Numerous studies have suggested that AGEs play an important role in the structural and functional alteration which occurs during aging and in chronic disease. Additionally, advanced glycosylation endproducts are noted to form more rapidly in diabetic and other diseased tissue than in normal tissue.

The "family" of AGEs includes species which can be isolated and characterized by chemical structure, some being quite stable, while others are unstable or reactive. The reaction between reducing sugars and the reactive groups of proteins may initiate the advanced glycosylation process. This process typically begins with a reversible reaction between the reducing sugar and the susceptible group on a protein for instance, to form a Schiff base, which proceeds to rearrange to yield the covalently-bonded Amadori rearrangement product. Once formed, the Amadori product undergoes further non-enzymatic rearrangements and reactions to produce the AGE-modified compound.

Recently, it has been reported that the in vivo oxidation of lipids is in some instances initiated by the reaction of lipids to form lipid-AGE and low density lipoproteins (LDL)-AGE (International Publication No. WO 93/13421 by Bucala et al.). More particularly, as the in vivo oxidation of lipids is related to the onset and course of atherosclerosis, the measurement of lipid-AGE and/or LDL-AGE levels in mammals represents a method for diagnosing the likelihood or onset of atherosclerosis, or measuring the course or severity of the disease, or the efficacy of anti-AGE treatments. Detection of lipid-AGE or LDL-AGE (in particular, ApoB-AGE) can be used to diagnose or monitor diabetes, as well as for monitoring serum LDL and cholesterol levels.

Antibodies Reactive With AGEs

Efforts have been made to develop antibodies to in vivo-formed AGEs. For example, Nakayama et al. (1989, Biochem. Biophys. Res. Commun. 162:740-745) studied protein-bound AGEs and in particular, raised antisera against keyhole limpet hemocyanin (KLH)-AGE in guinea pigs. These antisera exhibited high affinity binding, and the serial dilution curves of bovine serum albumin (BSA)-AGE, human serum albumin (HSA)-AGE and ribonuclease (RNase)-AGE were noted to parallel each other, suggesting that a structure in common among these AGE-modified proteins is recognized by the antisera. Treatment of AGEs with a reducing agent did not diminish immunoreactivity, suggesting that the antiserum recognized an AGE, rather than a Schiff base or Amadori product. However, Nakayama et al. do not report the ability of their antisera to bind to in vivo-produced AGEs, or the production of a monoclonal antibody having such properties.

Horiuchi et al.(1991, J. Biol. Chem. 266:7329-32) prepared polyclonal and monoclonal antibodies against bovine serum albumin-BSA. These antibodies were reported to recognize AGE-modified proteins formed in vitro. Treatment of these AGE-modified proteins with a reducing agent had no effect on immunoreactivity. In a later publication (Araki et al., 1992, J. Biol. Chem. 267:10211-14), these antibodies were purportedly analyzed for purposes of determining reactivity with lens crystallin protein-AGEs. Makita et al. (1992, J. Biol. Chem. 267:5133-38) reported development of a polyclonal rabbit antiserum, which was the first identification of development of antibodies reactive with in vivo-produced AGEs (see International Publication No. WO 93/13421, which is incorporated herein by reference in its entirety). In particular, Makita et al. demonstrated the ability of a rabbit RNase-AGE antiserum to bind to tissues from diabetic individuals and to serum components known to contain elevated levels of AGEs. A later publication (Makita et al., 1992, "Hemoglobin-AGE: A Circulating Marker of Advanced Glycosylation." Science 258:651-653) reported the ability of these antibodies to detect AGE-modified hemoglobin. The ability to measure AGE-modified hemoglobin is meaningful in detecting the presence of diabetes mellitus and the degree of glycemic control in diabetic patients, which is important for monitoring the long term course of this disease, to detect the intensification or worsening of such conditions, or alternatively, the improvement or lessening of the condition, as such may occur spontaneously or in conjunction with treatment. Bucala et al. (1993, Proc. Natl. Acad. Sci. USA 90:6434-38) reported that the rabbit anti-RNase-AGE antibodies were also reactive with lipid-AGEs formed in vivo. Although the development of polyclonal sera reactive with in vivo-formed AGEs finally led to the ability to detect AGEs in biological samples, there remains a need in the art for monoclonal antibodies reactive with in vivo-produced AGEs.

There is a further need in the art for a monoclonal antibody with higher affinity binding to AGEs or for specific AGEs than is demonstrated by the currently available polyclonal antibodies.

The citation of references herein shall not be construed as an admission that such is prior art to the present invention.

SUMMARY OF THE INVENTION

The present invention is directed to a monoclonal antibody, or an antigen-binding fragment thereof, reactive with in vivo-produced advanced glycosylation endproducts (AGEs), particularly where such monoclonal antibodies or antigen binding fragments thereof demonstrate an immunological binding characteristic of monoclonal antibody 4G9 as produced by hybridoma 4G9, deposited with the American Type Culture Collection (ATCC) and assigned Accession Number CRL 11626.

More particularly, said monoclonal antibody or antigen-binding fragment thereof can have an immunological binding characteristic, which characteristic is selected from the group consisting of reactivity with serum-AGE proteins, serum lipid-AGEs, serum-AGE peptides, LDL-AGE and collagen-AGE.

In a preferred aspect, the monoclonal antibody is humanized or a chimeric human-murine antibody. Therapeutic compositions including the antibody or active fragments thereof, or agonists and cognate molecules, or alternately, antagonists of the same, and methods of use of such compositions in the prevention, diagnosis or treatment of disease using these compositions are also included, wherein an effective amount of the composition is administered to a patient in need of such treatment.

The antigen-binding fragment of the monoclonal antibody can be a single chain Fv fragment, an F(ab') fragment, an F(ab) fragment, and an F(ab')$_2$ fragment, or any other antigen-binding fragment.

In a specific embodiment, infra, the monoclonal antibody or fragment thereof is a murine IgG isotype antibody; more particularly, the monoclonal antibody or fragment thereof can be monoclonal antibody 4G9 as produced by hybridoma 4G9, deposited with the American Type Culture Collection (ATCC) and assigned Accession Number CRL 11626.

Naturally, the invention extends to a hybridoma that produces monoclonal antibody 4G9, which hybridoma is deposited with the ATCC and assigned Accession Number CRL 11626.

The monoclonal antibody of the invention advantageously binds to in vivo-produced AGEs. Accordingly, in another aspect, the invention is directed to a method for detecting the presence of advanced glycosylation endproducts (AGEs) in a biological sample. The method comprises contacting a sample suspected of containing AGEs with the monoclonal antibody or antigen binding fragment thereof of the invention under conditions which allow for the formation of reaction complexes comprising the monoclonal antibody or antigen binding fragment thereof and the AGEs; and detecting the formation of such reaction complexes comprising the monoclonal antibody or antigen binding fragment thereof and AGEs in the sample. Detection of the formation of reaction complexes indicates the presence of AGEs in the sample.

In one embodiment, sample molecules may be allowed to bind or adhere to a solid support and the AGE-modified molecules so immobilized may be recognized by formation of reaction complexes with the monoclonal antibody of the present invention or an antigen-binding fragment thereof, through subsequent assay steps to detect reaction complexes.

In a further embodiment, the monoclonal antibody or antigen-binding fragment thereof is bound to a solid phase support, for instance as the first component of a "sandwich-type" assay for AGE-modified molecules reactive with the immobilized monoclonal antibody of the present invention, or an antigen-binding fragment thereof, wherein the second immunological binding partner may be a polyclonal or a monoclonal antibody, or a mixture thereof, including without limitation the monoclonal antibody of the present invention. In a further embodiment, the sample is contacted with a labelled advanced glycosylation endproduct (AGE), and unbound substances are removed prior to detecting the formation of reaction complexes in a competitive assay format. Formation of reaction complexes with the sample is detected by observing a decrease in the amount of labelled AGE bound in the assay. Alternatively, the formation of reaction complexes can be observed by detecting the binding of a labelled anti-AGE antibody or an antibody to an AGE carrier, such as but not limited to albumin, hemoglobin, low density lipoprotein, and the like, to the complex of the monoclonal antibody or antigen-binding fragment thereof and the AGE.

In another embodiment, an AGE is bound to a solid phase support. In a further aspect, the sample is contacted with said immobilized AGE bound to the solid phase support, in the presence of the monoclonal antibody of the present invention or an antigen-binding fragment thereof. The monoclonal antibody or antigen-binding fragment thereof is labelled either directly or by further assay steps using available reagents that specifically recognize the monoclonal antibody of the present invention or an antigen-binding fragment thereof. Formation of reaction complexes with AGE-modified molecules in the sample is detected by observing a decrease in the amount of label complexed to the solid phase support.

The methods for detecting the presence of AGEs in a sample according to the invention are useful for evaluating the level of AGEs in a biological sample. Accordingly, the invention is further directed to a method for evaluating the level of AGEs in a biological sample, which comprises detecting the formation of reaction complexes in a biological sample; and evaluating the amount of reaction complexes formed, which amount of reaction complexes corresponds to the level of AGEs in the biological sample.

The level of AGEs in a sample can have a strong diagnostic or prognostic value. Accordingly, the invention is further directed to a method for detecting or diagnosing the presence of a disease associated with elevated AGE levels in a mammalian subject comprising evaluating the level of AGEs in a biological sample from a mammalian subject; and comparing the level detected to a level of AGEs normally present in the mammalian subject. An increase in the level of AGEs as compared to normal levels indicates a disease associated with elevated levels of AGEs. Similarly, the invention relates to a method for monitoring the course of a disease associated with elevated AGE levels in a mammalian subject comprising evaluating the level of AGEs in a series of biological samples obtained at different times from a mammalian subject. An increase in the level of AGEs over time indicates progression of the disease, and a decrease in the level of AGEs over time indicates regression of the disease. Also, the invention relates to a method for monitoring a therapeutic treatment of a disease associated with elevated AGE levels in a mammalian subject comprising evaluating the levels of AGEs in a series of biological samples obtained at different times from a mammalian subject undergoing a therapeutic treatment for a disease associated with elevated AGE levels. A decrease in the level of AGEs over time indicates an effective therapeutic outcome.

The invention advantageously provides convenient test kit formats for practicing the foregoing methods. Accordingly, the invention provides a test kit for measuring the presence or amount of in vivo-derived AGEs in an analyte. Such a kit can comprise a monoclonal antibody of the invention or an antigen-binding fragment thereof of the invention; means for detecting the formation of reaction complexes between the monoclonal antibody or antigen-binding fragment thereof and AGEs; other reagents; and directions for use of the kit. In one embodiment, the test kit can further comprise preparation of an AGE or AGEs, or molecules modified by an AGE or AGEs, recognized by the monoclonal antibody, e.g., wherein said AGE molecules are irreversibly associated with a solid phase. In another embodiment, the test kit can further comprise a labelled anti-AGE antibody or antigen-binding fragment thereof, which labelled anti-AGE antibody is reactive with in vivo-produced AGEs, or directly reactive with the analyte molecule whose degree of AGE-modification is to be determined, including for instance a labelled anti-low density lipoprotein antibody.

Thus, a primary object of the invention is to provide a monoclonal antibody reactive with in vivo-produced AGEs.

A further object of the invention is to provide an indefinite source of an antibody reactive with in vivo-produced AGEs, which antibody has particular immunological binding characteristics that render it particularly useful for this purpose.

Yet a further object of the invention is to provide an assay for detecting low density lipoprotein-AGE, particularly ApoB-AGE.

A still further object of the invention is to provide therapeutic compositions and corresponding methods for treating conditions characterized by abnormal levels of AGEs which are based on or include the antibodies of the present invention.

These and other objects of the invention will be better understood by reference to the following drawings, detailed description of the invention, and the Examples.

DETAILED DESCRIPTION OF THE INVENTION

Figure 1:
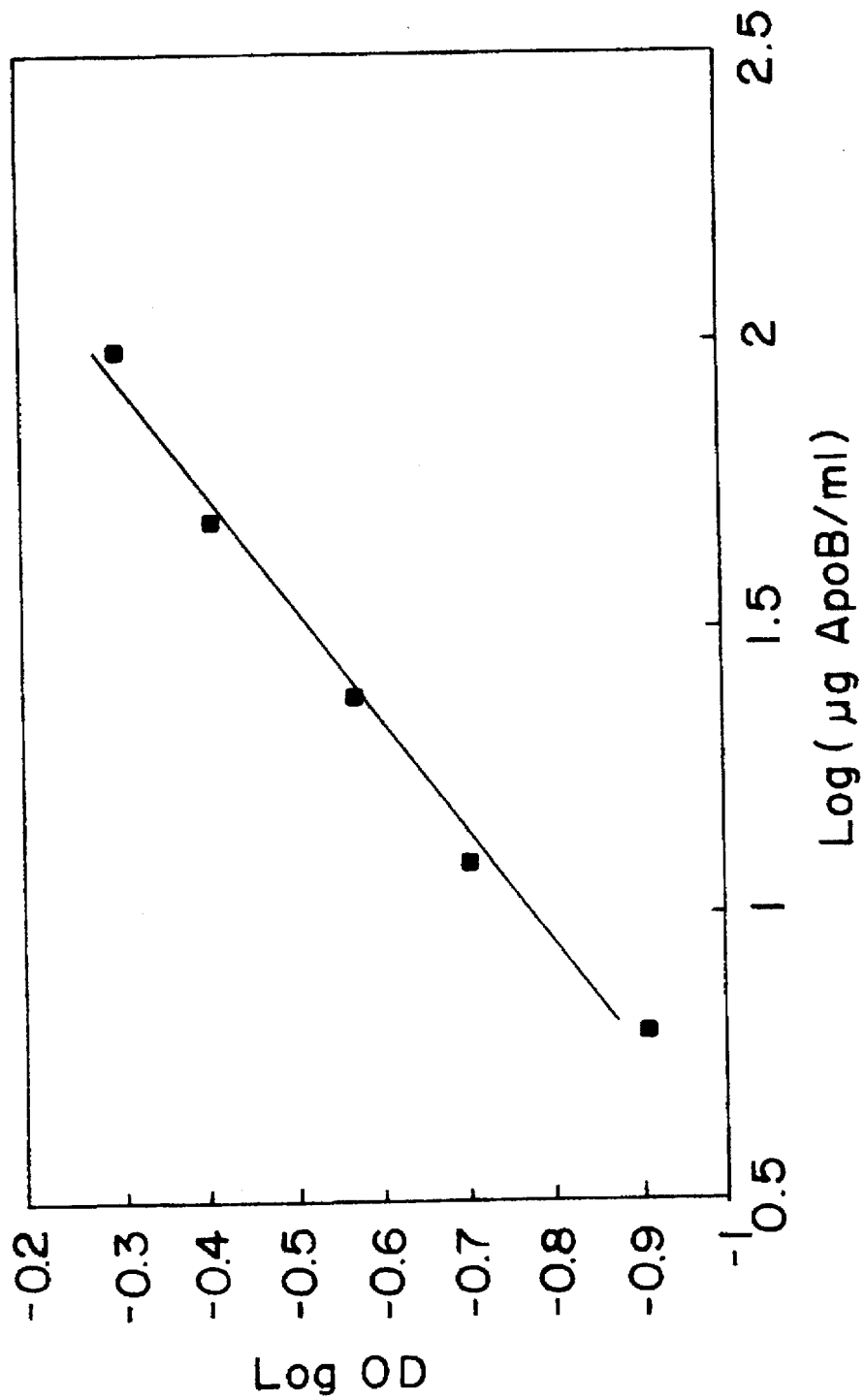
FIG. 1 is a graph demonstrating the recognition of LDL-AGE by means of the present invention.

The present invention is directed to a monoclonal antibody, or an antigen-binding fragment thereof, reactive with in vivo-produced advanced glycosylation endproducts (AGEs). In particular, said monoclonal antibody or antigen binding fragment thereof can demonstrate the immunological binding characteristics of monoclonal antibody 4G9 as produced by hybridoma 4G9, deposited with the American Type Culture Collection (ATCC) and assigned Accession Number CRL 11626. Naturally, the invention extends to the hybridoma as well. Thus, the invention advantageously provides an indefinitely prolonged cell source of a monoclonal antibody of the invention: the hybridoma.

The invention further relates to diagnostic assay methods and kits that comprise the monoclonal antibody of the invention and to therapeutic methods based thereon.

Various terms are used herein, which have the following meanings:

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10, amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

Where present, the term "immunological binding characteristics," or other binding characteristics of an antibody with an antigen, in all of its grammatical forms, refers to the specificity, affinity, cross-reactivity, and other binding characteristics of an antibody.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, and potentially useful human adjuvants such as BCG (bacille Calmette-Guerin) and *Corynebacterium parvum*. Preferably, the adjuvant is pharmaceutically acceptable.

The present invention advantageously provides methods for preparing monoclonal antibodies having the binding characteristics of monoclonal antibody 4G9 by immunizing with an antigen such as Rnase-AGE, lysozyme-AGE, BSA-AGE and KLH-AGE. Any such antigen may be used as an immunogen to generate antibodies with the immunological characteristics of monoclonal antibody 4G9. Such antibodies include but are not limited to monoclonal, chimeric, single chain, Fab fragments, and an Fab expression library.

Various procedures known in the art may be used for the production of polyclonal antibodies corresponding to the monoclonal antibody of the present invention. For example, reproduction of antibody may proceed by the immunization of various host animals. In this embodiment, the antigen may be conjugated to an immunogenic carrier, e.g., bovine serum albumin (BSA) or keyhole limpet hemocyanin (KLH), or the carrier may be reacted with a reducing sugar such as glucose such that the carrier bears AGE determinants. Various adjuvants such as those set forth above, may be used to increase the immunological response, depending on the host species.

For production of monoclonal antibodies of the present invention, any technique that provides for the production of antibody molecules by continuous cell lines in culture may be used. These include but are not limited to the hybridoma technique originally developed by Kohler and Milstein (1975, Nature 256:495–497), as well as the trioma technique, the human B-cell hybridoma technique (Kozbor et al., 1983, Immunology Today 4:72), and the EBV-hybridoma technique to produce human monoclonal antibodies (Cole et al., 1985, in *Monoclonal Antibodies and Cancer Therapy*, Alan R. Liss, Inc., pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, Proc. Natl. Acad. Sci. U.S.A. 80:2026–2030) or by transforming human B cells with EBV virus in vitro (Cole et al., 1985, in *Monoclonal Antibodies and Cancer Therapy*, Alan R. Liss, pp. 77–96). In fact, according to the invention, techniques developed for the production of "chimeric antibodies" or "humanized antibodies" (Morrison et al., 1984, J. Bacteriol. 159–870; Neuberger et al., 1984, Nature 312:604–608; Takeda et al., 1985, Nature 314:452–454) by splicing the genes from a mouse antibody molecule of the present invention, e.g., monoclonal antibody 4G9, together with genes from a human antibody molecule of appropriate biological activity can be used; such antibodies are within the scope of this invention. Chimeric antibodies are those that contain a human Fc portion and a murine (or other non-human) Fv portion; humanized antibodies are those in which the murine (or other non-human) complementarity determining regions (CDR) are incorporated in a human antibody; both chimeric and humanized antibodies are monoclonal. Such human or humanized chimeric antibodies are preferred for use in in vivo diagnosis or therapy of human diseases or disorders (described infra), since the human or humanized antibodies are much less likely than xenogeneic antibodies to induce an immune response, in particular an allergic response.

According to the invention, techniques described for the production of single chain antibodies (U.S. Pat. No. 4,946,778) can be adapted to provide single chain antibodies of the present invention. An additional embodiment of the invention utilizes the techniques described for the construction of Fab expression libraries (Huse et al., 1989, Science 246:1275–1281) to allow rapid and easy identification of monoclonal Fab fragments with the desired specificity for the antibody of the present invention, or its derivatives, or analogs.

Antibody fragments which contain the idiotype of the antibody molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, and the Fab fragments which can be generated by treating the antibody molecule with papain and a reducing agent. Such antibody fragments can be generated from any of the polyclonal or monoclonal antibodies of the invention; preferably, such antibody fragments are generated using monoclonal antibody 4G9.

In the production of antibodies, screening for the desired antibody can be accomplished by techniques known in the art, e.g., radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or other reagent to the primary antibody. In a further embodiment, the secondary antibody is labeled. Many means are known in the art for detecting binding in an immunoassay and are within the scope of the present invention. For example, to select antibodies in accordance with the present invention, one may assay generated hybridomas for a product which binds to in vivo-formed or in vitro-formed AGEs. Alternatively, such an antibody can be selected on the basis of an ability to compete for binding of monoclonal antibody 4G9 to such AGEs.

The foregoing antibodies can be used in methods known in the art relating to the localization and activity of AGE-modified proteins or tissues, e.g., for Western blotting, ELISA, detecting AGE-modified tissue in situ, measuring levels of AGE-modified molecules, for instance including proteins, peptides, lipids and nucleic acids, and, in particular, hemoglobin-AGE, immunoglobulin-AGE, and LDL-AGE, in appropriate physiological samples, such as serum samples.

Using the present invention, one can assess and/or detect the presence of stimulated, spontaneous, or idiopathic pathological states in mammals, by measuring the corresponding presence of advanced glycosylation endproducts. More particularly, the presence or amount of the AGEs may be followed directly by assay techniques such as those discussed herein, for example through the use of an appropriately labeled quantity of the present anti-AGE monoclonal antibody, as set forth herein.

The tissue and end organ damage caused by advanced glycosylation accumulates over a period of months to years. Diabetic complications progress over a similar duration, so that it is advantageous to detect earlier the AGE accumulation that has been linked to the development of pathology in such disease states.

In particular, the monoclonal antibody of the invention can be used to detect the presence of AGEs such as but not limited to, hemoglobin-AGE, albumin-AGE, lipid-AGEs, and AGE-modified peptides. Generally, the presence of a disease or disorder associated with AGEs can be assessed by detecting higher levels of AGEs in a biological sample from a subject who suffers from such a disease or disorder, as compared to a normal individual. The effectiveness of an agent, e.g., aminoguanidine, to prevent or inhibit the formation of AGEs can be evaluated by observing a decrease in the level of AGEs in biological samples obtained from a subject over a time interval.

For example, Hb-AGE has been determined to account for about 0.42% of circulating human hemoglobin. This fraction increases to approximately 0.75% in patients with diabetes-induced hyperglycemia. Of significance, diabetic patients treated for 28 days with aminoguanidine, an inhibitor of AGE formation in vivo, show significantly decreased levels of Hb-AGE at the end of the treatment period (International Publication No. WO 93/13421).

The present invention also extends to the measurement of other AGEs and particularly serum and urinary AGE-modified proteins and AGE-modified peptides. Serum and urinary AGE-modified peptides, like lipid-AGE and Hb-AGE, represent circulating markers of AGE accumulation that reflect the onset and extent of pathologies and other dysfunctions where such accumulation is a characteristic. Thus, those AGE-related and diabetic conditions where increased levels of AGEs have been observed, such as, for example, atherosclerosis, cataracts and diabetic nephropathy, may be monitored and assessed over the long term by the measurement of these AGEs, particularly by resort to the diagnostic methods disclosed herein.

Similarly, serum peptide-AGEs can be used as an indicator that reflects glomerular filtration rate (GFR) and kidney damage. Urinary peptide-AGEs may be used as an indicator to measure the turnover in tissue proteins, and more particularly, tissue protein bearing AGE modifications.

In the LDL-AGE, Hb-AGE, and the serum peptide-AGE assays, a blood sample is drawn and a separation procedure can be used. For measuring the level of LDL- or lipid-AGEs, a procedure such as that described in International Publication No. WO 93113421 by Bucala et al. can be used. For detecting hemoglobin-AGE, the cellular blood components can be separated from the serum, and hemoglobin can be extracted from the red blood cells. The serum level of LDL-AGE, peptide-AGEs and the presence or extent of Hb-AGEs present can then be evaluated.

By conducting these tests with a single blood sample, a broader time frame at which blood glucose levels become uncontrolled can be estimated, e.g., a 60 day range predictable by Hb-AGE for instance, extends the period to be assessed for glycemic control to before the 3–4 week time frame which is measured by $Hb-A_{1c}$ determination. If desired, the analyses of Hb-AGE and serum peptide-AGEs can be run together with a glucose level determination in blood or urine, a glucose tolerance test, and other tests useful for assessing diabetes control including the measurement of urinary peptide-AGEs, to give a complete patient profile.

In a preferred aspect of the invention, LDL-AGEs are measured using the monoclonal antibody of the invention in combination with either an anti-LDL (such as, but not limited to, anti-ApoB) antibody or a polyclonal anti-AGE antibody (such as rabbit anti-RNase-AGE).

Another aspect of the invention addresses advanced glycosylation endproducts which can be detected in the urine. Proteins, including peptides, are excreted in the urine in very low amounts in normal individuals, and at elevated levels in diseased individuals. The presence and/or level of urinary peptide-AGEs reflective of the turnover of tissue AGEs can be determined, correlated to and predictive of particular diseases or conditions.

The presence of peptides in the urine may be a symptom of numerous diseases or conditions reflective of a net catabolic state as would exist when the host or patient is undergoing invasion as by infection. Under such circumstances, the host mobilizes against the invasive stimulus by the secretion of numerous factors such as cytokines that suspend the anabolic energy storage activity and cellular repair activities and promote instead the catabolic depletion of energy stores and the recruitment of leukocytes and other factors to fight and neutralize the stimulus. The measurement of urinary peptide-AGEs provides yet another index of possible invasive activity in the host, such as cachexia and shock. Thus, one can measure the presence or level of peptide-AGEs in urine, and correlate this level to a standard. In normal individuals, the normal level may be low. In diabetic patients, the level of peptide-AGEs may be greater. Alternatively, in a subject suffering from AGE-associated advanced renal disease, the level of urinary peptides may be greatly decreased owing to the onset of renal failure. In patients experiencing infection or other trauma, the level of peptide-AGEs may be significantly greater than in normal individuals. Thus, the advancement or worsening of diabetes prior to the onset of renal complications, the onset of renal complications associated with diabetes or other AGE-related diseases, or the presence of infection could be detected by detecting urine levels of peptide-AGEs.

The anti-AGE monoclonal antibody of the invention can also be used in the treatment of patients to reduce the level or accelerate the removal of circulating AGEs or AGE-modified molecules, or similar such AGEs or AGE-modified molecules, which may be present in abnormally elevated levels in certain tissues, e.g., pancreas, liver, kidney or brain, and which AGEs may be undesired.

Additionally, it is within the scope of the invention described herein to utilize the anti-AGE monoclonal antibody for the design, screening and/or potentiation of drugs or compounds which are useful for treating elevated levels of AGEs in vivo. In this connection, the anti-AGE monoclonal antibody may be used to purify proteins that have been specially cultivated or, produced for use as therapeutic agents. The therapeutic use of such proteins is increasing in prominence and importance, and such exogenous proteins (like the host's own tissue and circulating proteins) are susceptible to glycation and the formation of AGEs. Such AGEs are chemically reactive and biologically active, so it is desirable to limit their introduction into a host during therapy. As a consequence, the present invention includes a method for purification of batches of such proteins by bringing them into contact with, for example, a quantity of the anti-AGE monoclonal antibody of the present invention or an antigen-binding fragment thereof, immobilized on a suitable substrate. In this way the glycosylated proteins could be separated from the rest of the batch by conventional procedures. The substrate could be refreshed or replaced periodically in the instance of a commercial process, so that a continuous circulation of protein material past the substrate and subsequent separation of the protein-AGE component could be conducted. Naturally, the foregoing scheme is presented for purposes of illustration only, and is capable of various modifications in design and execution within the skill of the art and the scope of the invention.

All of the protocols disclosed herein may be applied to the qualitative and quantitative determination of advanced glycosylation endproducts and to the concomitant diagnosis and surveillance of pathologies in which the accretion of advanced glycosylation endproducts is implicated. Such conditions as diabetes and the conditions associated with aging, such as atherosclerosis and skin wrinkling represent non-limiting examples, and accordingly methods for diagnosing and monitoring these conditions are included within the scope of the present invention.

The present invention also includes assay and test kits for the qualitative and/or quantitative analysis of the extent of the presence of advanced glycosylation endproducts. Such assay systems and test kits may comprise a labeled component prepared, e.g., by one of the radioactive and/or enzymatic techniques discussed herein, coupling a label to the anti-AGE monoclonal antibody of the present invention or an antigen-binding fragment thereof, or to a binding partner thereof. One of the components of the kits described herein is the anti-AGE monoclonal antibody of the present invention or the antigen-binding fragment thereof, in labeled or non-labeled form.

As stated earlier, the kits may be used to measure the presence of advanced glycosylation endproducts on recombinant or other purified proteins, and particularly those destined for therapeutic use, to assay them for AGE presence in a first instance, and in a second instance, to assist in their further purification free from material with undesired AGE modifications.

In accordance with the testing techniques discussed above, one class of such kits will contain at least the monoclonal antibody or an antigen-binding fragment thereof of the invention, means for detecting immunospecific binding of said antibody or fragment thereof to AGE components in a biological sample, and directions, of course, depending upon the method selected, e.g., "competitive", "sandwich", "DASP" and the like. The kits may also contain peripheral reagents such as buffers, stabilizers, etc.

More specifically, the preferred diagnostic test kit may further comprise a known amount of a binding partner to an anti-AGE antibody as described above, generally bound to a solid phase to form an immunosorbent, or in the alternative, bound to a suitable label.

A test kit of the invention may also further comprise a second antibody, which may be labelled or may be provided for attachment to a solid support (or attached to a solid support). Such an antibody may be, for example, an anti-AGE antibody, or an antibody specific for the non-AGE portion of the analyte to be assessed for AGE modification, or an AGE-component. Examples of the latter include, but are not limited to, anti-hemoglobin, anti-albumin, and, as shown herein, anti-ApoB. Such antibodies to the "carrier" portion of an AGE component can be polyclonal or monoclonal antibodies.

The present invention will be better understood by reference to the following Examples, which are illustrative of the invention, and are not intended as limiting of the invention. Where present, the designation "PBS" denotes phosphate-buffered saline. PBS may be prepared by dissolving 8.0 grams of NaCl, 0.2 grams of KCl, 1.44 grams of $Na_2HPO_4$, and 0.24 grams of $KH_2PO_4$ in 800 ml of distilled water, adjusting the pH to 7.2, and the volume to 1 liter. The resulting solution may be dispensed in convenient volumes and sterilized by autoclaving, and may be stored at room temperature. Likewise, the terms "Wash Solution" and "TBS-T Wash Solution" where present refer to the following: Tris Buffered Saline-Tween (TBS-T) (0.01M Trizma, 0.15M NaCl, 0.05% Tween-20, 0.02% sodium azide, adjusted to pH 7.4 with HCl). The term "Assay Buffer" refers to a solution generally containing 25 mM–1 M borate, pH 8.0, 150 mM NaCl, 0.01% EDTA and 1% BSA. The concentrations of the components comprising the Assay Buffer as may appear in the Examples listed below may vary within the scope of the present invention. Naturally the foregoing formulations are illustrative and may vary within the skill of the art, and are presented herein in fulfillment of the duty to present the best mode for the practice of the invention.

EXAMPLE 1

A HYBRIDOMA THAT SECRETES AN AGE—SPECIFIC MONOCLONAL ANTIBODY

The present Example describes production of a monoclonal antibody that reacts with in vivo-produced AGEs.

Preparation of Immunogen

One gm of KLH (Sigma Cat.#2133) was combined with 96 gm glucose in 500 ml of a 400 mM sodium phosphate buffer, pH 7.4. The solution was deoxygenated by bubbling nitrogen into the solution, and filter sterilized by passing the solution through a 0.2 micron cellulose acetate filter. After incubation at 37° C. for 90 days, the solution was dialyzed against a 20 mM sodium phosphate buffer, containing 0.15 M NaCl, pH 7.4. The protein content was determined using a Lowry assay, again filter sterilized, and aliquoted. The aliquots were stored at –80° C. until used.

Immunization Schedule

Five mice were pre-bled and earmarked. Each mouse was immunized subcutaneously with 0.2 ml of a preparation containing 100 µg of AGE modified-KLH in PBS (Immunogen) mixed 1:1 with Complete Freund's Adjuvant (CFA). Mice were boosted subcutaneously at day 21 with 0.2 ml of 50 µg of Immunogen in Incomplete Freund's Adjuvant (IFA). A second boost of 50 µg of Immunogen in IFA was administered on day 41 as before. Finally, a third boost of 50 µg of Immunogen in IFA was administered on day 63 as before and a test bleed taken from the tail vein and serum prepared. The mouse showing the highest titer as determined in the Antisera Test Bleed Titering procedure described below was selected and boosted intravenously with 0.1 ml containing 50 µg of Immunogen without adjuvant. Three days later, the spleen was removed and the animal exsanguinated.

Antisera Test Bleed Titering

An initial dilution of 1/100 of each serum sample to be titered was prepared in PBS containing 0.1% BSA, followed by 10 serial 2-fold dilutions in the same buffer for titer determination. Pre-immune sera noted above were diluted in the same manner as the immune sera and used as controls. Microtiter wells were coated with 1.5 µg of BSA-AGE antigen prepared by incubating bovine serum albumin (BSA) from Calbiochem, Catalog #12657, as described by Makita et al., J. Biol. Chem., 267(8), pp. 5133–5138 (1992). The antigen coated wells were sealed with Mylar sealing tape (Corning) and incubated overnight at 4° C. The microtiter plates were subsequently washed 6 times with TBS-T Wash Solution and blocked for one hour at 37° C. by adding 200 ul of a solution of PBS containing 0.2% BSA and 0.2% sodium azide. The microtiter plates were washed as before and 100 ul of the dilutions of pre-immune and immune sera were added. After incubation for 2 hrs. at room temperature, the microtiter plates were washed as described above and 100 ul of a goat anti-mouse IgG (gamma chain specific) horseradish peroxidase-conjugated antibody (Sigma) was added to all wells and incubated for 1 hr. at 37° C. The microtiter plates were washed as before and 100 ul of OPD Peroxidase Substrate (Sigma) was added to all wells and incubated for 30 minutes at room temperature. After the incubation period, the plates were read at 450 nm on a microtiter plate reader.

Hybridoma production was carried out by fusing the mouse spleen cells with the myeloma X63AG8.653 cell line as described elsewhere (Harlow, E. and D. Lane, Antibodies: A Laboratory Manual, Cold Spring Harbor Laboratory, 1988).

Hybridoma Screening Procedure

After fusion of spleen cells with the myeloma cell line, 1 drop of the 50 ml fusion mixture was added to each of 96 wells in 10 microwell cell culture plates (Corning). The plates were numbered 1 to 10, the rows of each plate by letter, and the columns by number to give a coding system that identified the parental cell cultures that developed from each drop of the fusion mixture. After culture in selection media described in Harlow and Lane, supra., hybridoma cultures were screened for antibody production to AGE antigen as follows:

BSA-AGE coated wells were prepared as described in the Antisera Test Bleed Titering section above. Further, BSA was coated on wells following the same coating procedure as with BSA-AGE to detect any nonspecific binding. The antigen coated plates were used to screen cell culture supernates from each of the parental cultures. The parental supernates were diluted 1:2 in PBS containing 0.2% BSA and 100 µl of each added to one well of a BSA-AGE coated microtiter plate and to one well of a BSA coated plate. The plates were incubated at room temperature for 2 hours and subsequently washed 6 times with TBS-T Wash Solution. One hundred µl of a goat anti-mouse IgG (gamma chain specific) horseradish peroxidase-conjugated antibody diluted 1:1000 in PBS containing 1% BSA was added to each well and the procedure followed as in the Antisera Test Bleed Titering section above. Sixteen parental cultures were found to produce absorbance readings exceeding 0.3 O.D. on the BSA-AGE wells and no reactivity on the BSA coated wells. The latter parental cultures were expanded in culture in 24 well macrowell plates (Corning) and upon further supernatant/antibody evaluation, three parental cultures were re-cloned (secondary cloning). Following a procedure described in Harlow and Lane, supra., the parental cultures were diluted in RPMI 1640 culture medium containing 20% fetal bovine serum to give a cell density of 0.5–10 cells per well on wells that were precultured with splenocyte feeder cells.

After two weeks only one parental cell culture, designated 5D2, yielded 17 AGE-specific producing antibody clones identified by testing the culture supernates in the screening procedure above. The other two parentals did not yield any positive subclones. After expansion of the 17 clones of 5D2 in cell culture, one clonal culture was selected that had high viability and produced the highest titer antibody to BSA-AGE in the aforementioned antibody screening assay. A further subcloning of the latter was done to assure monoclonality and the resultant clone designated 4D6 (5D2-4D6). A tertiary cloning of 5D2-4D6 was done as above, and 10 subclones were identified that produced good titers to BSA-AGE from the 0.3 cells/well dilution. One was selected from this group designated 4G9 (5D2-4D6-4G9) based on a comparative affinity analysis in accordance with Macdonald et al. (Macdonald, R. A. et al. 1988. Journal of Immunological Methods, 106:191–194). The cells from each culture were prepared in accordance with Harlow and Lane, supra. for frozen storage. 4G9 was expanded in culture and adapted to a protein-free medium (MaxiCell/Hybridoma-PF Medium, Cat. No. N10105, Atlanta Biologicals, Norcross, Ga.) for monoclonal antibody production.

EXAMPLE 2

BINDING AND IMMUNOLOGICAL CHARACTERISTICS OF THE AGE-SPECIFIC MONOCLONAL ANTIBODY 4G9

The ability of monoclonal antibody, mAb 4G9, raised against KLH non-enzymatically glycated by prolonged incubation with glucose (KLH-AGE) to recognize a variety of the non-enzymatically glycated proteins and peptides produced by browning with various sugars was determined.

Materials and Methods

Production of AGE proteins. All proteins and peptides were browned with glucose, ribose or glucose 6-phosphate in 300 mM sodium phosphate buffer, pH 7.4, for 8–12 weeks at 37° C. The control proteins were treated the same way except the sugars were omitted. Direct ELISA and competition ELISA. For direct ELISA, BSA-AGE or modified BSA was coated on microtiter plates, the unbound sites were blocked by incubation with Assay Buffer (25 mM borate, pH 8.0, 150 mM NaCl, 0.01% EDTA and 1% BSA). The plate was washed 6X and increasing concentrations of mAb in Assay Buffer were added. After this incubation, the plate was again washed and incubated with alkaline-phosphatase labeled goat anti-mouse antibodies (Cappel, Durham, N.C.) diluted 1:1000 in Assay Buffer. The unbound antibodies were removed by extensive washing and the bound antibodies were detected by addition of p-nitrophenylphosphate in recording the optical density at 410 nm.

The competition ELISA was performed by pre-coating microtiter plates with BSA-AGE and blocking with Assay Buffer. The plate was washed and mAb 4G9 and increasing concentrations of the competitors listed in Table 1 were added and simultaneously incubated for 1 hr at 37° C. The unbound materials were removed by extensive washing and the bound mAb was detected with alkaline phosphatase labeled anti-mouse antibodies similar to direct ELISA. All washes were in TBS-T wash solution; all incubations proceeded for 1 hr at 37° C.

Results

Interaction of mAb 4G9 with various browned compounds. Monoclonal antibody 4G9 (described in Example 1, above) displayed a broad range of recognition of proteins and peptides which were browned, i.e. incubated to acquire AGE modification, with different sugars. Table 1 shows a series of examples of the browned compounds which bound with this mAb in the competition assay indicating that AGE structures are important antigenic determinants for this antibody. The mAb showed no significant binding to any unglycated protein nor to any sugars assayed in the same manner as the glycated species.

TABLE 1

| protein or peptide | sugar | $IC_{50}$ M |
| --- | --- | --- |
| BSA | glucose | $3 \times 10^{-9}$ |
| Rat serum albumin | glucose-6-phosphate | $5 \times 10^{-9}$ |
| Hemoglobin | ribose | $2 \times 10^{-9}$ |
| Arg-lys | glucose | $2.5 \times 10^{-4}$ |
| Arg-lys | ribose | $5 \times 10^{-5}$ |
| Gly-lys | ribose | $5 \times 10^{-4}$ |
| lys | glucose | $5 \times 10^{-4}$ |
| 6-aminocaproic acid | glucose | $5 \times 10^{-4}$ |

1—$IC_{50}$ were from competition ELISA based on the concentration of the original proteins or peptides.
2—$IC_{50}$ for proteins, peptides or sugars alone > $10^{-2}$ M Discussion Thus, this monoclonal antibody recognizes AGEs on different proteins, peptides and amino acids, which AGEs arise from reaction with different reducing sugars. The antibody of the present invention specifically recognizes several glycated proteins in human and rat blood, indicating the presence of AGE structures in physiological fluid and in tissues.

EXAMPLE 3

ABILITY TO RECOGNIZE LDL-AGE IN HUMAN SERA AND PLASMA

In this example, LDL (low-density lipoprotein)-AGE in human sera/plasma samples pretreated to select for LDL was measured by using a combination of antibodies directed towards AGEs and LDL. The addition of polyethylene glycol (PEG) to samples selectively precipitates LDL and thereby improved detection of LDL-AGE. This assay provides for determining levels of AGE formation on LDL without detection of other AGE complexes that might be present in the blood. To determine levels of AGE on LDL complexes, LDL from human sera or plasma samples was selectively precipitated using 6–10% PEG and redissolved in buffer containing 1% SDS detergent. The samples were diluted in Assay Buffer and used in the sandwich protocol described in Materials and Methods below. The assay detects the presence of AGEs on LDL by capturing AGE-modified molecules through binding to immobilized monoclonal antibody 4G9, and then detects captured LDL-AGE complexes by using an anti-ApoB antibody.

Materials and Methods

Levels of LDL-AGE were measured using an ELISA sandwich assay. One hundred µl of serum or plasma were diluted in PBS containing PEG (6% final concentration) in a final volume of 1 ml and allowed to stand for 10 minutes. To obtain LDL, samples were centrifuged at 14000 r.p.m. for 5 minutes and the supernatant was discarded. The LDL pellet was dissolved in 50 µl of PBS containing 1% SDS and allowed to stand overnight at room temperature. Next, 950 µl of Assay Buffer comprising 1% BSA, 50 ml of 1M borate solution, 0.01% EDTA in 950 ml PBS, pH 8.0, was added.

The LDL-AGE assay was performed using 50 µl of sample per well. The wells were pre-coated with mAb 4G9 by adding 100 µl per well of mAb 4G9 diluted 1:10 in PBS and incubated overnight at 4° C. Antibody coating solutions were removed and the plate was washed 6 times with TBS-T Wash Solution. The plate was then blocked with Assay Buffer in PBS, 200 µl per well, and incubated for one hour at 37° C. Assay Buffer was then removed and the plate washed 6 times with TBS-T Wash Solution. Fifty µl of Assay Buffer was added to each well prior to addition of sample. Eighty µl of a 5 mg/ml stock solution of naturally occurring AGE-modified LDL purified from human blood (Cappel Company, #59392) was dissolved in 100 µl of a PBS solution containing 1% SDS and allowed to stand for 30 minutes. This solution was then diluted with 1.82 ml of Assay Buffer to give a 200 µg/ml standard stock solution. The stock solution was then serially diluted 2-fold to obtain standard solutions in the range of 50–3.12 µg/ml.

The samples and standards were incubated on the plate for 1 hour at 37° C. and then washed 6 times as before. AGE-specific LDL binding was detected using horseradish peroxidase conjugated-antibody against ApoB protein (Biodesign International, Kennebunk, Me.) diluted 1:500 in Assay Buffer and incubated for 1 hour at 37° C. The addition of the OPD substrate (Sigma Chemical, St. Louis, Mo.) allowed visualization of detected complexes at 450 nm.

Results

The results are presented in FIG. 1 which shows the normal human LDL-AGE dilution curve as detected with 4G9 monoclonal antibody.

EXAMPLE 4

ABILITY TO RECOGNIZE IgG-AGE IN HUMAN SERA AND PLASMA

Detection of AGE-modified molecules in blood provides evidence for the onset or progress of diseases associated with this phenomenon. This example demonstrates detection of IgG-AGE in human sera/plasma with monoclonal antibody 4G9.

Figure 2:
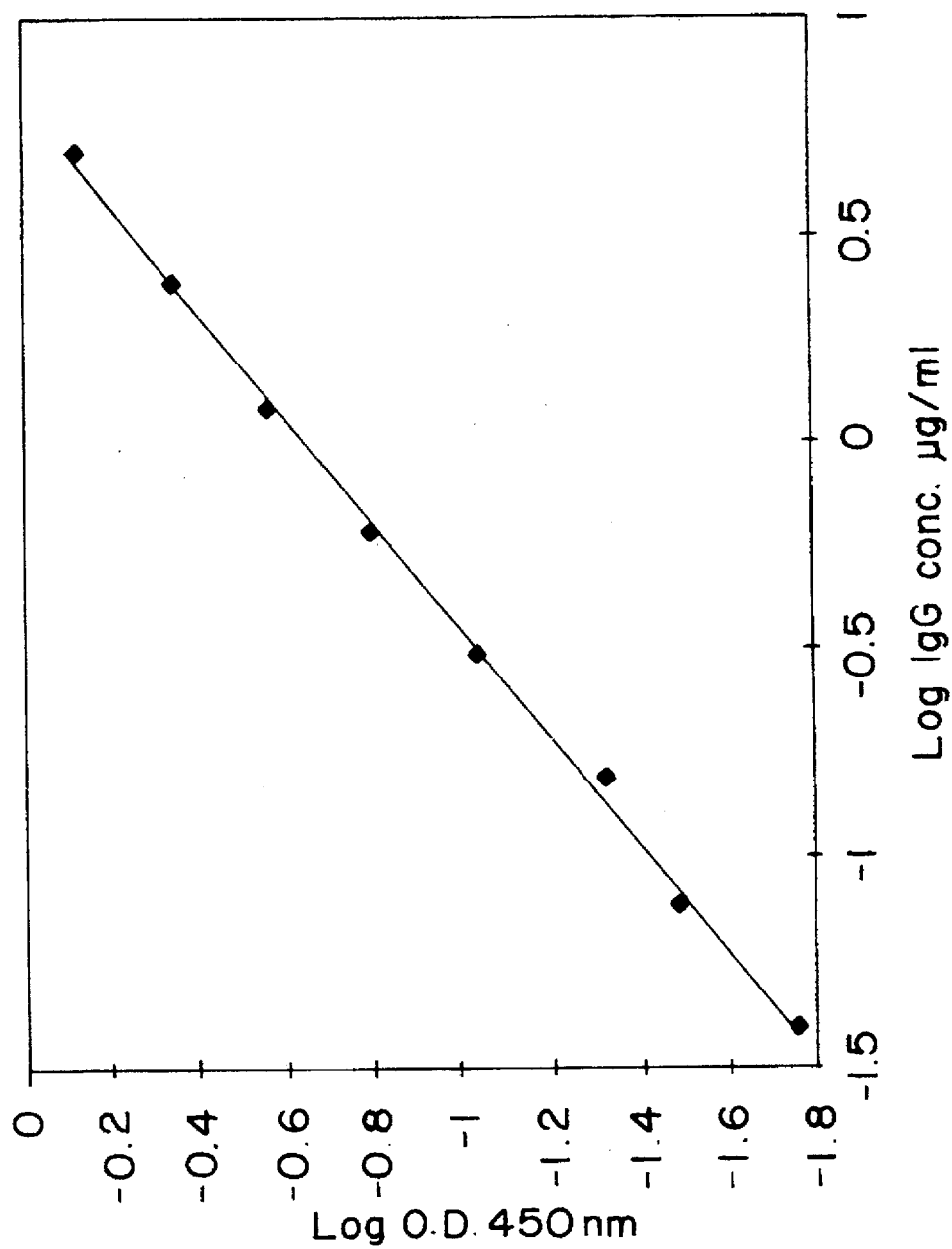
FIG. 2 depicts a graph showing the detection of IgG-AGE complexes in serum by means of the present invention.

To determine levels of IgG-AGE, dilutions of serum samples were made in Assay Buffer and applied to the 4G9-coated wells. Horseradish peroxidase (HRP)- conjugated goat anti-human IgG then acts as a detector antibody. Color development produced by the enzymatic conversion of OPD, a substrate for HRP, is measured to indicate the amount of AGE present. FIG. 2 shows the results of his procedure.

Materials and Methods

Levels of AGE were measured using an ELISA sandwich assay described as follows. The wells were coated with mAb 4G9 by adding 100 µl per well of mAb 4G9 in protein-free media diluted 1:10 in PBS and incubated overnight at 4° C. Antibodies were removed and the plate was washed 6x with TBS-T Wash Solution containing 0.05% Tween 20. The plate was then blocked with Assay Buffer (1% BSA, 50 mM borate, 0.01% EDTA in PBS), 200 µl per well, and incubated for one hour at 37° C. The Assay Buffer was then removed and the plate washed as before. Fifty µl of Assay Buffer was added to each well prior to addition of sample. Naturally occurring AGE modified human IgG (Sigma Chemical, St Louis, Mo.) was diluted in Assay Buffer to give a range of concentrations from 25 ng/ml to 5.25 µg/ml and used as a standard. The IgG-AGE assay was performed using 50 µl of sample per well.

The IgG-AGE solutions were incubated on the plate for 1 hour at 37° C. and then washed. Bound AGE was detected using horseradish peroxidase conjugated goat anti-human IgG (Sigma Chemical, St. Louis, Mo.) diluted 1:500 in Assay Buffer and incubated for 1 hour at 37° C. The addition of the OPD substrate (Sigma Chemical, St. Louis, Mo.) allowed visualization of detected complexes at 450 nm.

Results

FIG. 2 shows the normal human serum IgG dilution curve. This data, as well as the LDL-AGE results of Example 3, show that 4G9 detects AGE modifications formed on proteins in vivo.

EXAMPLE 5

DETECTION OF SERUM-AGE PEPTIDE LEVELS

The use of the monoclonal antibody of the present invention as an indicator of conditions where increased levels of AGEs are likely to be detected was explored with respect to the analysis of serum-AGE peptide levels. More particularly, the ability to detect increased levels of serum-AGE peptides was investigated utilizing the present monoclonal antibody. Thus, serum from 10 normal and 10 diabetic subjects was diluted 1:3 in PBS and was subjected to fractionation through an Amicon Microcon 10 microconcentrator according to the manufacturer's instructions. Thus, 50 µl of the ultrafiltrate containing low molecular weight molecules, including for instance, peptides of less than 10,000 molecular weight, was added to microtiter wells that had been coated with BSA-AGE in a competitive ELISA assay procedure as described in Makita et al. (1992), J. Biol. Chem. 267(8):5133–5138. This procedure was varied, however, in the following fashion:

1. The wash solution was TBS-T Wash Solution as described earlier herein;

2. The primary antibody used was the 4G9 monoclonal antibody of the present invention;

3. The secondary antibody used was a goat anti-mouse IgG conjugated to alkaline phosphatase (Cappel) and incubated at 37° C. for 45 minutes. Thereafter, the wells were washed 6 times with TBS-T Wash Solution and 100 µl of PNPP substrate (Sigma #N2507, St. Louis, Mo.) diluted in diethanolamine buffer made according to the substrate manufacturer's package insert was added and incubated for 30 minutes. The OD of the reaction product was measured at 410 nm in a Dynatech MR5000 microtiter plate reader.

Figure 3:
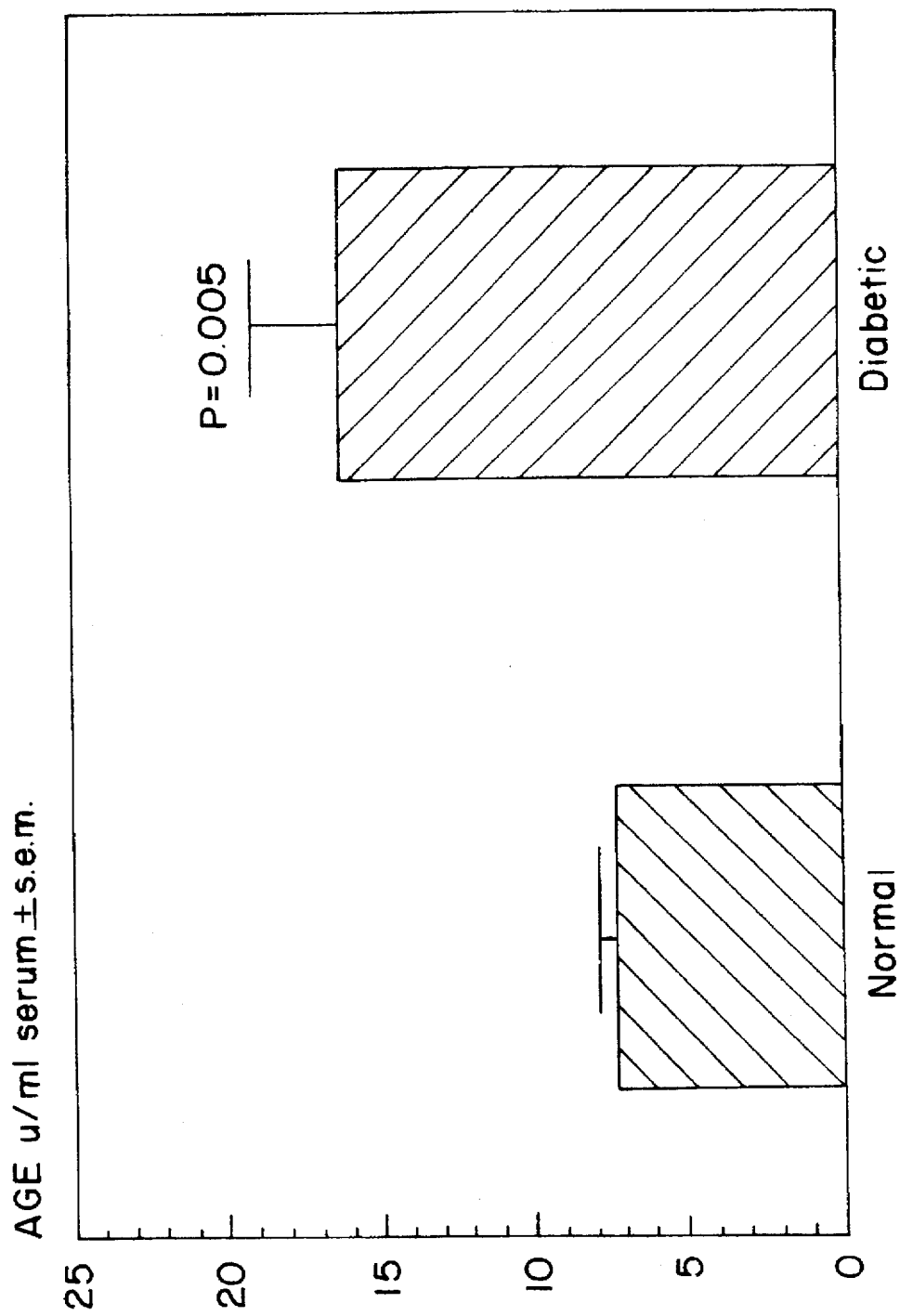
FIG. 3 is a graph depicting the detection and measurement of serum peptide-AGE levels in normals and diabetics by means of the present invention.

The values were expressed per milliliter of serum, and are shown in FIG. 3.

EXAMPLE 6

DETECTION AND MEASUREMENT OF URINARY AGE LEVELS IN RATS

Figure 4:
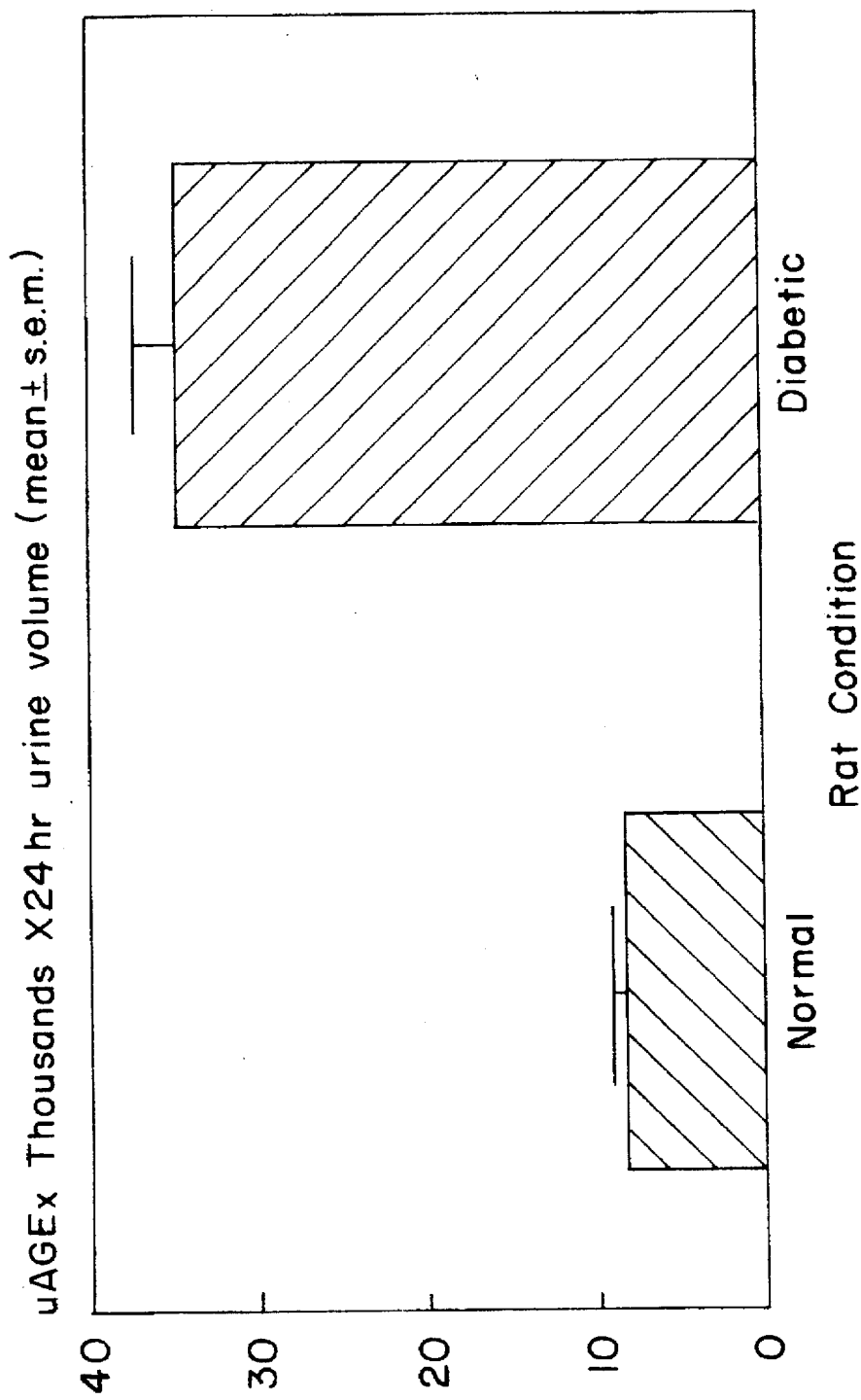
FIG. 4 is a graph depicting the results of the detection and measurement of urinary AGE levels by means of the present invention.

Urinary AGE levels were examined in rats, likewise utilizing as part of the diagnostic kit and protocol, the monoclonal antibody of the present invention. Thus, urine collected from rats housed in metabolic cages was centrifuged at 14,000 rpm for 10 minutes to remove debris, diluted 1:30 in PBS and subsequently passed through an Amicon Microcon 10 microconcentrator using the procedure according to the manufacturer's instructions. Fifty µl of the ultrafiltrate that contains, among other small molecules, peptides of less than 10,000 MW, was added to microtiter wells that had been coated with BSA-AGE in the competitive ELISA assay procedure described in Makita et al., and modified as described in Example 5, above. After substrate incubation for approximately 1 hour, the wells were read in a microtiter plate reader at 410 nm. The values were expressed as AGE U/ml (defined in WO 93/13421 by Bucala) of urine per daily volume of urine collected in ml, and the results are set forth in FIG. 4.

EXAMPLE 7

DETECTION AND MEASUREMENT OF AGE LEVELS IN RAT SKIN

In this example, an assay of levels in rat skin was conducted. Accordingly, a two square-inch of rat skin was trimmed to remove connective tissue and muscle. The epidermis and dermis of the skin sample were separated from each other, and the dermis was then minced into small pieces. The tissue was dried overnight in a Speed Vac (Speed Vac Plus, SC210A, Savant Instruments), and the following day the dried tissue was disaggregated using a spatula. The resulting tissue was then delipidated using 5 ml of 1:1 chloroform/methanol (3 times). The supernatants were discarded, and the tissue pellet then dried for a period of 2 hours in a Speed Vac. A 1 mg/ml solution of collagenase in PBS (Collagenase-B - Boehringer-Mannheim) was then prepared. A digestion reaction prepared at a concentration of 60 mg of dried tissue per 1 mg of collagenase, with 20 µl of toluene per ml to prevent contamination.

The sample thus prepared was then agitated at 37° C. for 48 hours in a glass tube, after which it was centrifuged at 12,000 rpm at 4° C. for 20 minutes in a plastic tube. The supernatant was then transferred to an Eppendorf tube and heated at 70° C. for 1 hour, after which it was again centrifuged at 12,000 rpm at room temperature, and the supernatant was collected. The sample was then subjected to pepsin digestion using 200 micrograms of pepsin in 0.01N HCl per 1 ml of sample. The pH of the sample was adjusted to 2.0 using 12N HCl. The sample was thereafter incubated in a water bath at 37° C. for 30 minutes. 6 N NaOH was utilized to adjust the sample pH to 7.0.

Figure 5:
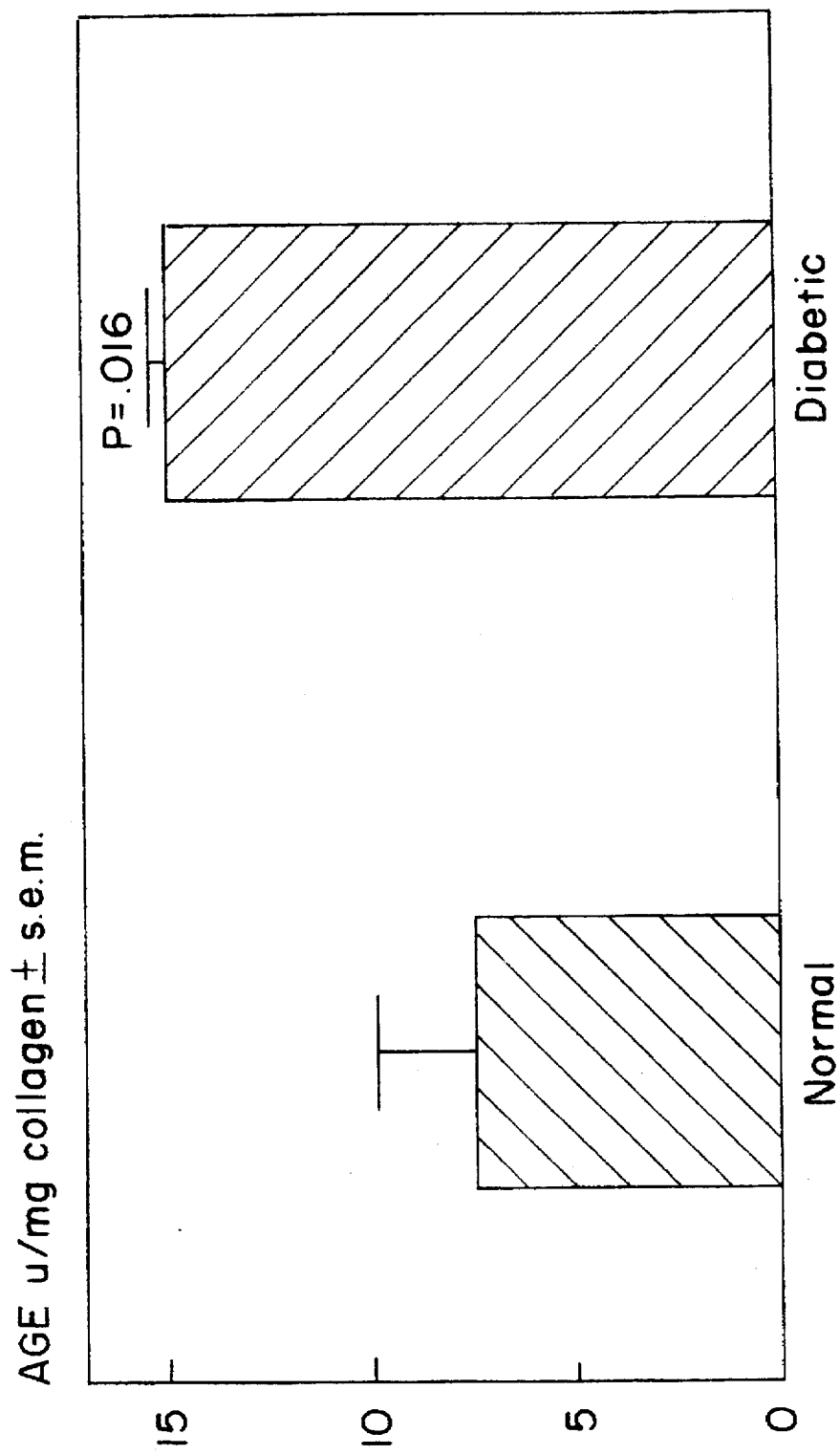
FIG. 5 is a graph depicting the results of the measurement of collagen-AGE levels in rat skin by means of the present invention.

The sample was then fractionated using an Amicon Microcon 10 microconcentrator and the ultrafiltrate was then analyzed in a competitive assay (Makita et al.) in accordance with the present invention for AGE content. The hydroxyproline (collagen) content was analyzed according to the procedure of Stegmann, H. and Stalder, K., Clin. Chim. Acta 18:267–271 (1967). The sample values are expressed in AGE U/mg (defined in WO 93/13421 by Bucala) collagen and are set forth in FIG. 5.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

What is claimed is:

1. A method for detecting the presence of advanced glycosylation endproducts (AGES) in a biological sample comprising the steps of:
   a) contacting a sample suspected of containing AGEs with a monoclonal antibody or antigen binding fragment thereof under conditions which allow for the formation of reaction complexes comprising the monoclonal antibody or antigen binding fragment thereof and the AGEs; and
   b) detecting the formation of reaction complexes comprising the monoclonal antibody or antigen binding fragment thereof and AGEs in the sample;
   wherein detection of the formation of reaction complexes indicates the presence of AGEs in the sample, and wherein the monoclonal antibody or antigen-binding fragment thereof is monoclonal antibody 4G9 as produced by hybridoma 4G9, deposited with the American Type Culture Collection (ATCC) and assigned Accession Number CRL 11626.

2. The method of claim 1 wherein the monoclonal antibody or antigen binding fragment thereof is bound to a solid phase support.

3. The method of claim 2 which further comprises contacting the sample with a labelled advanced glycosylation endproduct (AGE) in step (a), and removing unbound substances prior to step (b), and wherein the formation of reaction complexes in the sample is detected by observing a decrease in the amount of labelled AGE in the sample.

4. The method of claim 2, wherein the formation of reaction complexes is observed by detecting the binding of a labelled anti-AGE antibody to the complex of the monoclonal antibody or antigen binding fragment thereof and the AGE.

5. The method of claim 4, wherein the labeled antibody demonstrates an immunological characteristic selected from the group consisting of cross-reactivity with serum-AGE proteins, serum-AGE lipids, serum-AGE peptides, LDL-AGE, Hb-AGE, and collagen-AGE.

6. The method of claim 1 wherein the monoclonal antibody or antigen binding fragment thereof is labelled.

7. The method of claim 1 wherein an AGE is bound to a solid phase support.

8. The method of claim 7, which further comprises contacting the sample with an AGE in step (a), and removing unbound substances prior to step (b), and wherein the monoclonal antibody or antigen binding fragment thereof is labelled and the formation of reaction complexes in the sample is detected by observing a decrease in the amount of label.

9. The method according to claim 1, wherein the AGE is an low density lipoprotein (LDL)-AGE.

10. A method for evaluating the level of AGEs in a biological sample comprising:
    (a) detecting the formation of reaction complexes in a biological sample according to the method of claim 1; and
    (b) evaluating the amount of reaction complexes formed, which amount of reaction complexes corresponds to the level of AGEs in the biological sample.

11. A method for detecting or diagnosing the presence of a disease associated with elevated AGE levels in a mammalian subject comprising:
    (a) evaluating the level of AGEs in a biological sample from a mammalian subject according to claim 10; and
    (b) comparing the level detected in step (a) to a level of AGEs normally present in the mammalian subject;
    wherein an increase in the level of AGEs as compared to normal levels indicates a disease associated with elevated levels of AGEs.

12. A method for monitoring the course of a disease associated with elevated AGE levels in a mammalian subject comprising evaluating the level of AGEs in a series of biological samples obtained at different time points from a mammalian subject according to the method of claim 10, wherein an increase in the level of AGEs over time indicates progression of the disease, and wherein a decrease in the level of AGEs over time indicates regression of the disease.

13. A method for monitoring a therapeutic treatment of a disease associated with elevated AGE levels in a mammalian subject comprising evaluating the levels of AGEs in a series of biological samples obtained at different time points from a mammalian subject undergoing a therapeutic treatment for a disease associated with elevated AGE levels according to the method of claim 10, wherein a decrease in the level of AGEs over time indicates an effective therapeutic outcome.

14. A method for detecting the onset and/or monitoring the course of diabetes comprising performing the method of any one of claims 11 to 13.

15. A test kit for measuring the presence or amount of AGEs in an analyte, comprising:
    a) a monoclonal antibody or an antigen binding fragment thereof, which monoclonal antibody or antigen binding fragment is monoclonal antibody 4G9 as produced by hybridoma 4G9, deposited with the American Type Culture Collection (ATCC) and assigned Accession Number CRL 11626;
    b) labeled AGE or a labeled secondary antibody which binds 4G9 (ATCC CRL 11626); and
    c) directions for use of the kit.

16. The test kit of claim 15, wherein the monoclonal antibody or antigen-binding fragment thereof which is characterized by an activity selected from the group consisting of reactivity with serum-AGE proteins, serum-AGE lipids, serum-AGE peptides, LDL-AGE and collagen-AGE.

17. The test kit of claim 15 wherein the anti-AGE antibody is irreversibly associated with a solid phase.

18. The test kit of claim 15 which further comprises a labelled anti-AGE antibody, which labelled anti-AGE antibody is reactive with in vivo-produced AGEs.

19. The test kit of claim 15 which further comprises a labelled anti-low density lipoprotein antibody.

20. The test kit of claim 15, wherein the low density lipoprotein is ApoB.

21. The test kit of claim 15 which further comprises a labelled AGE.

22. The test kit of claim 15 which further comprises an AGE.

23. The test kit of claim 22, wherein the AGE is bound to a solid phase and the antibody is labelled.

* * * * *